June 20, 1933. R. ENGLE Plant Pat. 69
CARNATION
Filed July 12, 1932
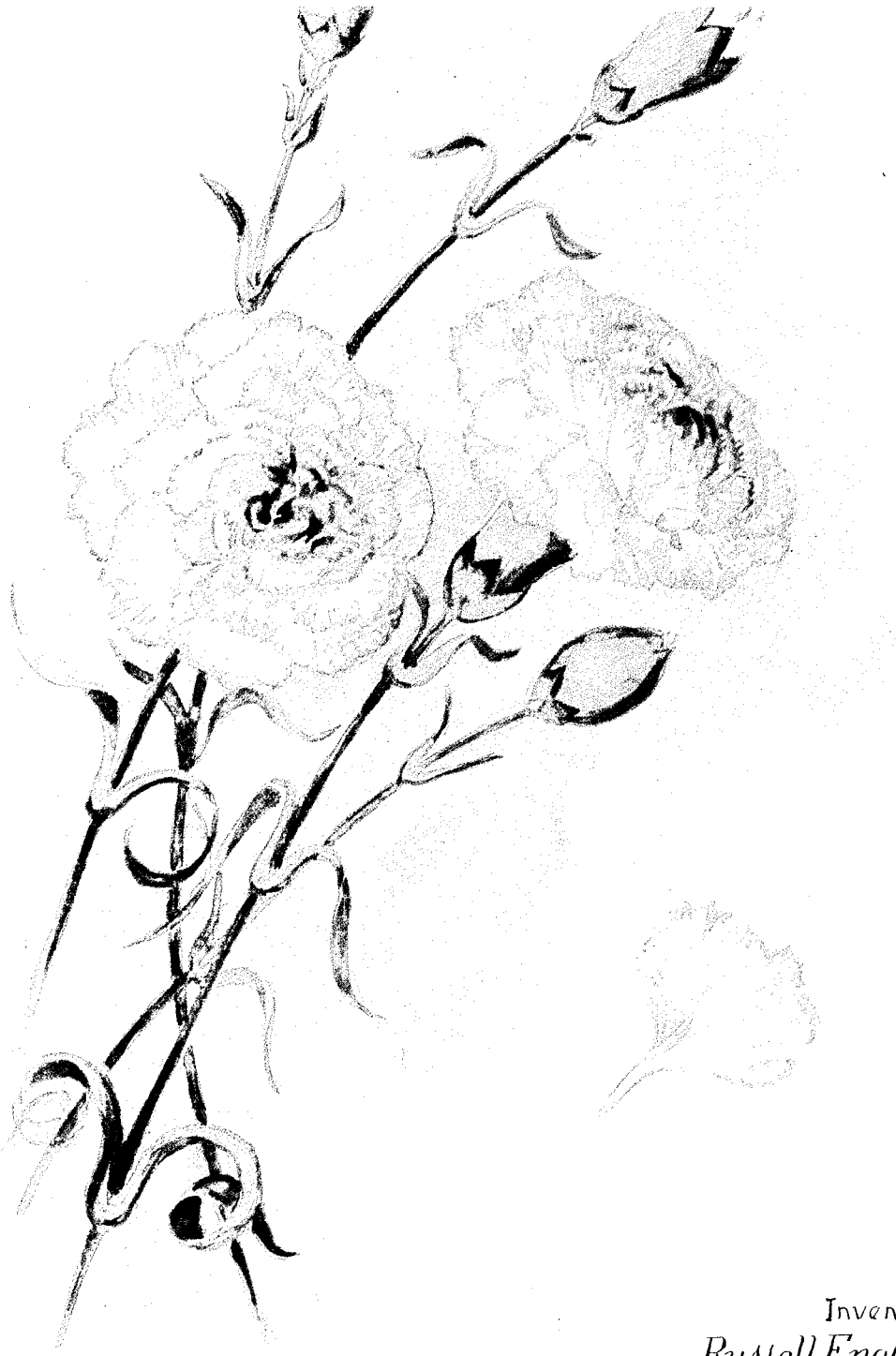
Inventor
Russell Engle
Attorney Patented June 20, 1933

Plant Pat. 69

UNITED STATES PATENT OFFICE

RUSSELL ENGLE, OF KOKOMO, INDIANA, ASSIGNOR TO THOMAS L. KNIPE, OF KOKOMO, INDIANA

CARNATION

Application filed July 12, 1932. Serial No. 622,153.

This invention relates to new and improved carnations the purpose being to provide a carnation having new and richer colors than are possessed by carnations heretofore known.

The drawing illustrates my new carnation in the several stages of flowering from the bud to the fully opened flower and showing also a single petal.

The carnation differs from known carnations in that the petals are striped with a rosy magenta, the edges of which petals have a delicate rosy magenta. The plant is a very prolific bloomer giving more blooms than the average carnation. The blooms are of fair size considering the number of blooms produced and average about 2 to 2½ inches across. The carnation was developed by hand cross breeding. The seed parent was an unnamed white seedling. The pollen parent was a reddish purple in color and generally known as "Royal". The new plant was raised from seed from the pollenized white seedling. The carnations are propagated asexually from cuttings from the original plant which cuttings come true to color. The propagation is in the usual manner of setting cuttings in some good rooting medium until the roots are formed.

Having thus fully described and illustrated my new plant, what I claim as new and desire to secure by Letters Patent, is:

A plant of the kind described characterized with blooms of the color shown having basically white petals, the edges of which are tinged with rosy magenta, the center petals being rather deep rosy magenta in color.

In witness whereof, I have hereunto set my hand at Kokomo, Indiana, this 21st day of June, A. D. nineteen hundred and thirty-two.

RUSSELL ENGLE.